United States Patent
Penta et al.

(10) Patent No.: US 11,854,058 B2
(45) Date of Patent: Dec. 26, 2023

(54) FOOTCARE PRODUCT DISPENSING KIOSK

(71) Applicant: Scholl's Wellness Company LLC, Parsippany, NJ (US)

(72) Inventors: Rama Penta, San Mateo, CA (US); Daniel Weick, Doylestown, NJ (US); Manikandan Sukumaran, Randolph, NJ (US); Hasan Ayoubi, Monroe Township, NJ (US); Kyeong Ho Park, Fort Lee, NJ (US); Howard Mendelowitz, Secaucus, NJ (US); Jay Matusow, South Nyack, NY (US)

(73) Assignee: Scholl's Wellness Company LLC, Parsippany, NJ (US)

( * ) Notice: Subject to any disclaimer, the term of this patent is extended or adjusted under 35 U.S.C. 154(b) by 560 days.

(21) Appl. No.: 16/753,764

(22) PCT Filed: Oct. 12, 2018

(86) PCT No.: PCT/US2018/055549
§ 371 (c)(1),
(2) Date: Apr. 4, 2020

(87) PCT Pub. No.: WO2019/075287
PCT Pub. Date: Apr. 18, 2019

(65) Prior Publication Data
US 2020/0294109 A1 Sep. 17, 2020

Related U.S. Application Data
(60) Provisional application No. 62/572,290, filed on Oct. 13, 2017.

(51) Int. Cl.
*A61B 5/107* (2006.01)
*G06Q 30/0601* (2023.01)
(Continued)

(52) U.S. Cl.
CPC ....... *G06Q 30/0631* (2013.01); *A61B 5/1036* (2013.01); *A61B 5/1074* (2013.01);
(Continued)

(58) Field of Classification Search
None
See application file for complete search history.

(56) References Cited

U.S. PATENT DOCUMENTS

| | | |
|---|---|---|
| 770,775 A | 9/1904 | Norris |
| 1,281,987 A | 10/1918 | McSweeney |
| (Continued) | | |

FOREIGN PATENT DOCUMENTS

| | | |
|---|---|---|
| CA | 2324967 A1 | 5/2002 |
| CN | 1344907 A | 4/2002 |
| (Continued) | | |

OTHER PUBLICATIONS

Ballester et al. ("Fast, portable and low-cost 3D foot digitizers: Validity and reliability of measurements." Proceedings of 3DBODY. TECH (2017): 11-12; Oct. 11-12, 2017) (Year: 2017).*
(Continued)

*Primary Examiner* — Christopher B Tokarczyk
(74) *Attorney, Agent, or Firm* — Lowenstein Sandler LLP

(57) ABSTRACT

A kiosk for providing footcare product recommendations comprises a base, a foot mat positioned in a recess in the base, a removable cover plate positioned over the recess for covering at least a portion of the foot mat, the cover plate comprising an opening leaving at least a portion of the foot mat uncovered, and one or more spacers located in the recess for positioning the foot mat in the recess.

9 Claims, 9 Drawing Sheets

(51) Int. Cl.
   *A61B 5/103* (2006.01)
   *A61B 5/00* (2006.01)
(52) U.S. Cl.
   CPC .......... *A61B 5/6892* (2013.01); *A61B 5/7435* (2013.01); *G06Q 30/0641* (2013.01)

(56) References Cited

U.S. PATENT DOCUMENTS

| | | |
|---|---|---|
| 2,043,187 A | 6/1936 | Owens |
| 2,055,072 A | 9/1936 | Everston |
| 2,063,625 A | 12/1936 | Rigandi |
| 2,107,620 A | 2/1938 | Rigandi |
| 2,157,026 A | 5/1939 | Sochor |
| 2,221,202 A | 11/1940 | Ratcliff |
| 2,446,448 A | 8/1948 | Whitman |
| 2,447,954 A | 8/1948 | Meldman |
| 2,464,023 A | 3/1949 | Carson |
| 2,863,231 A | 12/1958 | Jones |
| 2,975,519 A | 3/1961 | Berlin, Jr. |
| 3,066,417 A | 12/1962 | Samuels |
| 3,219,929 A | 11/1965 | King |
| 3,233,348 A | 2/1966 | Gilkerson |
| 3,328,882 A | 7/1967 | Blivice |
| 3,375,586 A | 4/1968 | Kennedy |
| 3,398,469 A | 8/1968 | Bressan |
| 3,457,647 A | 7/1969 | Cohen |
| 3,696,456 A | 10/1972 | Dunham |
| 3,828,792 A | 8/1974 | Valenta |
| 3,859,740 A | 1/1975 | Kemp |
| 4,124,946 A | 11/1978 | Tomlin |
| 4,168,585 A | 9/1979 | Gleichner |
| 4,267,728 A | 5/1981 | Manley et al. |
| 4,408,402 A | 10/1983 | Looney |
| 4,412,364 A | 11/1983 | Orea Mateo |
| 4,430,645 A | 2/1984 | Eskandry et al. |
| 4,449,264 A | 5/1984 | Schwartz |
| 4,494,321 A | 1/1985 | Lawlor |
| 4,510,636 A | 4/1985 | Phillips |
| 4,510,700 A | 4/1985 | Brown |
| 4,517,696 A | 5/1985 | Schartz |
| 4,520,581 A | 6/1985 | Irwin et al. |
| 4,538,353 A | 9/1985 | Gardner |
| 4,555,696 A | 11/1985 | Brown |
| 4,597,196 A | 7/1986 | Brown |
| 4,604,807 A | 8/1986 | Bock et al. |
| 4,648,923 A | 3/1987 | Chapnick |
| 4,656,344 A | 4/1987 | Mergenthaler et al. |
| 4,686,993 A | 8/1987 | Grumbine |
| 4,688,338 A | 8/1987 | Brown |
| 4,702,255 A | 10/1987 | Schenkl |
| 4,745,290 A | 5/1988 | Frankel et al. |
| D296,493 S | 7/1988 | Diaz |
| 4,760,654 A | 8/1988 | Limbach |
| 4,782,605 A | 11/1988 | Chapnick |
| 4,823,420 A | 4/1989 | Bartneck |
| 4,858,621 A | 8/1989 | Franks |
| RE33,066 E | 9/1989 | Stubblefield |
| 4,876,758 A | 10/1989 | Rolloff et al. |
| 4,901,390 A | 2/1990 | Daley |
| 4,917,105 A | 4/1990 | Tiitola et al. |
| 4,962,593 A | 10/1990 | Brown |
| 4,972,718 A | 11/1990 | Said et al. |
| 5,014,706 A | 5/1991 | Philipp |
| 5,015,427 A | 5/1991 | Sosnow |
| 5,025,476 A | 6/1991 | Gould et al. |
| 5,068,983 A | 12/1991 | Marc |
| 5,077,915 A | 1/1992 | Gross |
| 5,092,060 A | 3/1992 | Frachey et al. |
| 5,098,319 A | 3/1992 | McGaffigan et al. |
| 5,128,880 A | 7/1992 | White |
| 5,164,793 A | 11/1992 | Wolfersberger et al. |
| 5,168,634 A | 12/1992 | Misevich |
| 5,170,572 A | 12/1992 | Kantro |
| 5,175,946 A | 1/1993 | Tsai |
| 5,195,030 A | 3/1993 | White |
| 5,203,096 A | 4/1993 | Rosen |
| 5,206,804 A | 4/1993 | Thies et al. |
| 5,212,894 A | 5/1993 | Paparo |
| 5,216,594 A | 6/1993 | White et al. |
| 5,237,520 A | 8/1993 | White |
| 5,282,326 A | 2/1994 | Schroer, Jr. et al. |
| 5,299,454 A | 4/1994 | Fuglewicz et al. |
| 5,311,677 A | 5/1994 | Mann et al. |
| 5,317,819 A | 6/1994 | Ellis, III |
| 5,339,252 A | 8/1994 | White et al. |
| 5,341,819 A | 8/1994 | Hyvarinen |
| 5,361,133 A | 11/1994 | Brown et al. |
| 5,369,896 A | 12/1994 | Frachey et al. |
| 5,394,624 A | 3/1995 | Siepser |
| D357,349 S | 4/1995 | Vasyli |
| 5,408,543 A | 4/1995 | Yoshida |
| D358,249 S | 5/1995 | Vasyli |
| 5,435,077 A | 7/1995 | Pyle |
| 5,438,768 A | 8/1995 | Bauerfeind |
| 5,474,087 A | 12/1995 | Nashner |
| D367,164 S | 2/1996 | Fisher et al. |
| 5,498,590 A | 3/1996 | Burmeister et al. |
| 5,532,299 A | 7/1996 | Dubois |
| 5,542,196 A | 8/1996 | Kantro |
| 5,550,149 A | 8/1996 | Powell et al. |
| 5,563,423 A | 10/1996 | Wu et al. |
| 5,564,465 A | 10/1996 | Pettesch |
| 5,585,328 A | 12/1996 | Zimmerman et al. |
| 5,586,067 A | 12/1996 | Gross et al. |
| 5,611,153 A | 3/1997 | Fisher et al. |
| 5,640,779 A | 6/1997 | Rolloff et al. |
| 5,659,395 A | 8/1997 | Brown et al. |
| 5,671,055 A | 9/1997 | Whittlesey et al. |
| 5,671,362 A | 9/1997 | Cowe et al. |
| 5,746,011 A | 5/1998 | Hedstrom |
| 5,790,256 A | 8/1998 | Brown et al. |
| 5,804,571 A | 9/1998 | Schein |
| 5,822,873 A | 10/1998 | Meilman |
| 5,823,550 A | 10/1998 | Bennett et al. |
| 5,845,568 A | 12/1998 | Rosser, Jr. |
| 5,909,373 A | 6/1999 | Sansone et al. |
| 5,918,383 A | 7/1999 | Chee |
| 5,933,984 A | 8/1999 | Carlson et al. |
| 5,939,502 A | 8/1999 | DeSimone et al. |
| 5,945,610 A | 8/1999 | Galasso |
| 5,951,935 A | 9/1999 | Healy et al. |
| 5,957,870 A | 9/1999 | Yamato et al. |
| 5,979,067 A | 11/1999 | Waters |
| 5,987,982 A | 11/1999 | Wenman et al. |
| 5,989,700 A | 11/1999 | Krivopal |
| 6,000,147 A | 12/1999 | Kellerman |
| 6,038,793 A | 3/2000 | Kendall |
| 6,041,521 A | 3/2000 | Wong |
| 6,041,524 A | 3/2000 | Brooks |
| 6,125,557 A | 10/2000 | Brown |
| 6,131,311 A | 10/2000 | Brown et al. |
| 6,145,220 A | 11/2000 | Johnson, Jr. et al. |
| 6,160,264 A | 12/2000 | Rebiere |
| 6,163,971 A | 12/2000 | Humphries, Jr. et al. |
| 6,170,705 B1 | 1/2001 | Schneider et al. |
| 6,219,929 B1 | 4/2001 | Tasker et al. |
| 6,233,847 B1 | 5/2001 | Brown |
| 6,247,250 B1 | 6/2001 | Hauser |
| 6,269,555 B1 | 8/2001 | Brown |
| 6,282,816 B1 | 9/2001 | Rosendahl |
| 6,286,232 B1 | 9/2001 | Snyder et al. |
| 6,289,107 B1 | 9/2001 | Borchers et al. |
| 6,301,805 B1 | 10/2001 | Howlett et al. |
| 6,301,807 B1 | 10/2001 | Gardiner |
| 6,315,786 B1 | 11/2001 | Smuckler |
| 6,331,893 B1 | 12/2001 | Brown et al. |
| 6,345,455 B1 | 2/2002 | Greer, Jr. et al. |
| 6,430,831 B1 | 8/2002 | Sundman |
| 6,481,120 B1 | 11/2002 | Xia et al. |
| 6,498,590 B1 | 12/2002 | Dietz et al. |
| 6,505,522 B1 | 1/2003 | Wilssens |
| 6,508,017 B1 | 1/2003 | DeBarro et al. |
| 6,519,874 B1 | 2/2003 | Dean |
| 6,532,299 B1 | 3/2003 | Sachdeva et al. |

(56) References Cited

U.S. PATENT DOCUMENTS

| | | | |
|---|---|---|---|
| 6,550,149 B2 | 4/2003 | Dowdell |
| 6,557,273 B2 | 5/2003 | Polifroni |
| 6,560,902 B1 | 5/2003 | Eschweiler |
| 6,563,423 B2 | 5/2003 | Smith |
| 6,564,465 B1 | 5/2003 | Ward |
| D475,184 S | 6/2003 | Polifroni |
| 6,585,328 B1 | 7/2003 | Oexman et al. |
| 6,594,922 B1 | 7/2003 | Mansfield et al. |
| 6,598,321 B2 | 7/2003 | Crane et al. |
| 6,601,320 B1 | 8/2003 | Brown |
| 6,604,301 B1 | 8/2003 | Manoli, II et al. |
| 6,611,195 B1 | 8/2003 | Manneschi et al. |
| 6,618,960 B2 | 9/2003 | Brown |
| 6,691,432 B2 | 2/2004 | Masseron |
| 6,802,138 B2 | 10/2004 | McManus et al. |
| 6,804,571 B2 | 10/2004 | Fullen et al. |
| 6,823,550 B2 | 11/2004 | Kantro |
| 6,845,568 B2 | 1/2005 | Ward |
| 6,854,199 B2 | 2/2005 | Polifroni |
| 6,909,373 B2 | 6/2005 | Power et al. |
| 6,931,763 B2 | 8/2005 | Bray, Jr. et al. |
| 6,939,502 B2 | 9/2005 | Lyden |
| 6,954,557 B2 | 10/2005 | Kim et al. |
| 6,964,205 B2 | 11/2005 | Papakostas et al. |
| 7,008,386 B2 | 3/2006 | Alaimo et al. |
| 7,089,152 B2 | 8/2006 | Oda et al. |
| 7,100,296 B2 | 9/2006 | Root |
| 7,120,958 B2 | 10/2006 | Copeskey et al. |
| D534,503 S | 1/2007 | Jung et al. |
| 7,421,808 B2 | 9/2008 | Baier et al. |
| 7,484,319 B2 | 2/2009 | Cheskin et al. |
| 7,617,068 B2 | 11/2009 | Tadin et al. |
| 7,742,633 B2 | 6/2010 | Huang et al. |
| 7,789,840 B2 | 9/2010 | Nole |
| 7,958,653 B2 | 6/2011 | Howlett et al. |
| 8,117,922 B2 | 2/2012 | Xia et al. |
| 8,170,705 B2 | 5/2012 | Koelling et al. |
| 8,406,454 B2 | 3/2013 | Bar |
| 8,800,169 B2 | 8/2014 | Howlett et al. |
| 9,038,482 B2 | 5/2015 | Xia et al. |
| 9,576,311 B2 | 2/2017 | Kia et al. |
| 2002/0050080 A1 | 5/2002 | Vasyli |
| 2002/0060630 A1 | 5/2002 | Power |
| 2002/0071597 A1 | 6/2002 | Ravitz et al. |
| 2002/0083618 A1 | 7/2002 | Erickson et al. |
| 2003/0009915 A1 | 1/2003 | Bacon |
| 2003/0061733 A1 | 4/2003 | Karsten |
| 2003/0037124 A1 | 5/2003 | Kantro |
| 2003/0079303 A1 | 5/2003 | Kantro |
| 2003/0140523 A1 | 7/2003 | Issler |
| 2003/0164954 A1 | 9/2003 | Gerhard et al. |
| 2004/0020078 A1 | 2/2004 | Thomas, Jr. et al. |
| 2004/0025376 A1 | 2/2004 | Grisoni et al. |
| 2004/0032052 A1 | 2/2004 | Meyers et al. |
| 2004/0143452 A1 | 7/2004 | Pattillo et al. |
| 2004/0168329 A1 | 9/2004 | Ishimaru |
| 2004/0181976 A1 | 9/2004 | Copeskey et al. |
| 2004/0194344 A1 | 10/2004 | Tadin |
| 2004/0221487 A1 | 11/2004 | Fried |
| 2004/0250359 A1 | 12/2004 | Spivey |
| 2004/0250508 A1 | 12/2004 | Pattillo et al. |
| 2005/0028109 A1 | 2/2005 | Richards et al. |
| 2005/0030372 A1 | 2/2005 | Jung et al. |
| 2005/0044751 A1 | 3/2005 | Alaimo et al. |
| 2005/0049816 A1 | 3/2005 | Oda et al. |
| 2005/0066545 A1 | 3/2005 | Peoples |
| 2005/0072892 A1 | 4/2005 | Fell |
| 2005/0108899 A1 | 5/2005 | Kielt et al. |
| 2005/0203712 A1 | 9/2005 | Lowe |
| 2005/0223604 A1 | 10/2005 | Neuner |
| 2005/0262733 A1 | 12/2005 | Dean |
| 2006/0098896 A1 | 5/2006 | Pishdadian et al. |
| 2007/0011173 A1 | 1/2007 | Agostino |
| 2007/0043582 A1 | 2/2007 | Peveto et al. |
| 2007/0055405 A1* | 3/2007 | Koelling ............ G05B 19/401 |
| | | 700/232 |
| 2007/0107261 A1 | 5/2007 | Cheskin et al. |
| 2007/0202478 A1 | 8/2007 | Al-Obaidi et al. |
| 2007/0253004 A1 | 11/2007 | Danenberg et al. |
| 2008/0097720 A1 | 4/2008 | Tadin et al. |
| 2008/0196273 A1 | 8/2008 | Kosta |
| 2009/0076772 A1* | 3/2009 | Hinshaw ............... A43D 1/025 |
| | | 36/43 |
| 2009/0240514 A1 | 9/2009 | Oexman et al. |
| 2010/0269371 A1 | 10/2010 | Gray |
| 2011/0247235 A1 | 10/2011 | de Roode et al. |
| 2012/0197161 A1* | 8/2012 | Xia ...................... A61B 5/1074 |
| | | 600/592 |
| 2012/0260525 A1 | 10/2012 | Kim |
| 2013/0053677 A1 | 2/2013 | Schoenfeld |
| 2013/0172787 A1 | 7/2013 | Marovets |
| 2014/0006451 A1* | 1/2014 | Mullis ................... G06Q 20/18 |
| | | 707/784 |
| 2014/0033829 A1 | 2/2014 | Xia et al. |
| 2014/0107966 A1 | 4/2014 | Xia et al. |
| 2014/0107967 A1 | 4/2014 | Xia et al. |
| 2014/0107968 A1 | 4/2014 | Xia et al. |
| 2014/0309534 A1 | 10/2014 | Pichler et al. |
| 2015/0088731 A1* | 3/2015 | Ackerman ......... G06Q 10/0836 |
| | | 705/39 |
| 2015/0223730 A1 | 8/2015 | Ferrantelli |

FOREIGN PATENT DOCUMENTS

| | | | | |
|---|---|---|---|---|
| CN | 2707063 Y | | 7/2005 |
| DE | 19923280 A1 | | 11/1999 |
| DE | 20119402 U1 | | 1/2002 |
| EP | 0119660 A1 | | 9/1984 |
| EP | 0173396 A2 | | 3/1986 |
| EP | 0534503 A2 | | 3/1993 |
| EP | 2241209 A1 | | 10/2010 |
| EP | 2430939 A1 | | 3/2012 |
| EP | 2430940 A1 | | 3/2012 |
| EP | 2430938 B1 | | 6/2018 |
| FR | 2776175 A1 | | 9/1999 |
| GB | 2349728 A | | 11/2000 |
| JP | H03247305 A | | 11/1991 |
| JP | H03251203 A | | 11/1991 |
| JP | H0518810 A | | 1/1993 |
| JP | H1124913 A | | 1/1999 |
| JP | 2001000207 A | * | 1/2001 | ............... A43D 1/02 |
| JP | 2001000207 A | | 1/2001 |
| JP | 2005192744 A | | 7/2005 |
| JP | 2007275307 A | | 10/2007 |
| NL | 9100591 A | | 11/1992 |
| SU | 1814877 | | 11/1992 |
| TW | 200525400 A | | 8/2005 |
| WO | 9723769 A1 | | 7/1997 |
| WO | 2008036397 A2 | | 3/2008 |
| WO | 2008036398 A2 | | 3/2008 |

OTHER PUBLICATIONS

International Search Report for Application No. PCT/US2018/055549 dated Apr. 1, 2019, 2 pages.

Menz, Hylton B., Alternative Techniques for the Clinical Assessment of Foot Pronation, Journal of the American Podiatric Medical Association, Mar. 1998, vol. 88, No. 3, pp. 119-129.

Torburn, Leslie, et al., "Assessment of Rearfoot Motion: Passive Positioning, One-Legged Standing, Gait," Foot & Ankle International, Oct. 1998, vol. 19, No. 10, pp. 688-693.

Wrobel, James S., "Reliability and Validity of Current Physical Examination Techniques for the Foot and Ankle," Journal of the American Podiatric Medical Association, May/Jun. 2008, vol. 98, No. 3, pp. 197-206.

McPoil, Thomas G., "Relationship Between Three Static Angles of the Rearfoot and the Pattern of Rearfoot Motion During Walking," Journal of Orthopedic & Sports Physical Therapy, Jun. 1996, pp. 370-375, vol. 23(6), Orthopaedic and Sports Physical Therapy Sections of the American Physical Therapy Association.

(56) References Cited

OTHER PUBLICATIONS

Cavanagh, Peter R., et al., The Arch Index: A Useful Measure From Footprints published in Journal of Biomechanics, Jan. 1987, pp. 547-551, vol. 20(5), Pergamon Press, New York, NY USA.
Chu, Woei Chyn, et al "The Use of Arch Index to Characterize Arch Height: A Digital Image Processing Approach" IEEE Transactions on Biomedical Engineering, Nov. 1995, pp. 1088-1093, vol. 42(11), IEEE Service Center, Piscataway, NJ USA.
Urry, Stephen R. and Wearing, Scott C., "Arch indexes from ink footprints and pressure platforms are different" published in "The Foot", Jun. 2005, pp. 68-73, vol. 15(2).
PCT Search Report for International Application No. PCT/US2007/020476 dated Sep. 4, 2008, 12 pages.
Davis, B.L., et al., "Decomposition of superimposed ground reaction forces into left and right force profiles", J. Biomechanics, (Apr. 1993) vol. 26, No. 4-5, pp. 593-597.
EP Search Report for EP11192771 dated Feb. 10, 2012, 8 pages.
EP Search Report for EP11192772 dated Feb. 10, 2012, 6 pages.
EP Search Report for EP10171065 dated Aug. 27, 2010, 7 pages.
EP Search Report for EP11192770 dated Feb. 10, 2012, 8 pages.
ROC (Taiwan) Search Report (English Translation) dated Mar. 19, 2014 for ROC (Taiwan) Patent Application No. 102123875; 1 page.
International Search Report for International Application No. PCT/US2015/025211 dated Jun. 29, 2015, 3 pages.
International Search Report for PCT/US2007/020475 dated Mar. 26, 2009, 19 Pages.
ROC (Taiwan) Search Report (Engish Translation) dated Apr. 24, 2014, for ROC (Taiwan) Patent Application No. 100113829; 1 page.
International Search Report and Written Opinion for International Application No. PCT/US2015/025211 dated Oct. 16, 2016, 13 pages.

\* cited by examiner

FOOTCARE PRODUCT DISPENSING KIOSK

REFERENCE TO RELATED APPLICATIONS

This application is a national stage entry under 35 U.S.C. § 371 of International Application No. PCT/US2018/055549, filed Oct. 12, 2018, which claims the benefit of U.S. Provisional Patent Application No. 62/572,290, filed Oct. 13, 2017, the disclosures of which are incorporated by reference herein in their entirety.

FIELD OF THE INVENTION

The present invention relates generally to footcare products, and more specifically to providing customized footcare products to a consumer.

BACKGROUND OF THE INVENTION

Conventional footcare products, such as orthotics, foot cushions, heel cups, etc., are typically sold from conventional retail displays. Although packaging may provide some guidance, customers may have to guess which products are appropriate, e.g., the customers' size, foot characteristics, and other attributes. However, even if a customer were given e opportunity to try on a product, the customer may not know the best type of support or size of footcare product for their particular foot characteristics, e.g., the arch type of the customer's foot. This practice may result in the customer buying multiple products before customer finally finds a product that meets the customer's needs.

Custom foot-care products may also be sold to provide a customer the proper level of support. Custom footcare products that have adjustable support, still may not be of the proper size for a customer's shoes and may require significant time to determine the proper size. Some custom footcare products are made by moldable material. However, this requires time to measure the foot and then a period of time to make the orthotic. Because these orthotics are custom-made, they are typically more expensive than pre-manufactured orthotics. Also, creating a custom molded orthotic generally requires a trained professional that measures the customer and makes or orders the orthotic.

SUMMARY OF THE INVENTION

According to some embodiments, a reconfigurable kiosk measures aspects of a user's foot and generates a footcare product recommendation for footcare products displayed by the kiosk. The reconfigurable design of the kiosk enables easy and inexpensive updating and enhancement of the kiosk over time. According to some embodiments, a kiosk includes reconfigurable foot mat sensor mounting that can accommodate foot mats of different sizes, allowing for foot mat designs and configurations to change over time. A system of spacers may be used to locate a foot mat within a base of the kiosk and different sizes and configurations of foot mats can be incorporated by changing spacer configuration. According to some embodiments, a kiosk includes a reconfigurable display area having multiple display mounts for mounting replaceable displays. Advertising or other product related information incorporated in a kiosk may be modified by swapping out a replaceable display with an updated display.

According to some embodiments, a kiosk for providing footcare product recommendations includes a base, a foot mat positioned in a recess in the base, a removable cover plate positioned over the recess for covering at least a portion of the foot mat, the cover plate comprising an opening leaving at least a portion of the foot mat uncovered, and one or more spacers located in the recess for positioning the foot mat in the recess.

In any of these embodiments, the foot mat may be configured to obtain pressure measurements at different points of a foot of a user. In any of these embodiments, the foot mat may comprise a sensor area for measuring a foot of a user, the opening in the cover plate may be at least large enough to leave the sensor area uncovered, and the one or more spacers may be configured to position the sensor area beneath the opening in the cover plate.

In any of these embodiments, the foot mat may include one or more foot shaped indicators for indicating to a user where to stand on the foot mat, the opening in the cover plate may be at least large enough to leave the one or more foot shaped indicators uncovered, and the one or more spacers may be configured to position the indicators beneath the opening in the cover plate.

In any of these embodiments, the one or more spacers may position the foot mat laterally within the recess. In any of these embodiments, the one or more spacers may control depth of the foot mat within the recess. In any of these embodiments, the kiosk may further include a display portion for displaying information related to footcare products.

In any of these embodiments, the kiosk may further include at least one processor in communication with the foot mat, the at least one processor configured to select a footcare product for a user based on measurements for the user generated by the foot mat. In any of these embodiments, the kiosk may further include an output device to display information received from the processor, including a footcare product recommendation for the user.

According to some embodiments, a kiosk for displaying products includes a base, a tower supported by the base, a product display portion mounted to the tower and configured for holding products, a display screen housed at least partially in an upper portion of the tower above the product display portion, and one or more display mounts extending from the tower and configured for removeably mounting replaceable displays.

In any of these embodiments, the base may be configured as a platform for a user to stand on. In any of these embodiments, the product display portion may include shelves for holding product. In any of these embodiments, the one or more display mounts may include a panel removeably mounted to a side of the tower and aligned with the display screen.

In any of these embodiments, the one or more display mounts may include a panel positioned between the product display portion and the monitor and the display panel may be angled upwardly. In any of these embodiments, the kiosk may further include a computing system located within the upper portion of the tower behind the monitor.

According to some embodiments, a method for updating a kiosk includes generating, by the kiosk, measurement data related to one or more physical attributes of a user via one or more sensors of the kiosk, generating, by the kiosk, a product recommendation based at least partially on the measurement data, transmitting product recommendation information and kiosk information to a server system over a network, determining a kiosk enhancement for the kiosk by analyzing at least a portion of the product recommendation information and at least a portion of the kiosk related information, and updating the kiosk with the kiosk enhancement.

In any of these embodiments, updating the kiosk with the kiosk enhancement may include modifying a display panel of the kiosk. In any of these embodiments, the product recommendation information may include user height, user weight, user age, user gender, or time of recommendation generation. In any of these embodiments, the kiosk information may include a kiosk identifier or a kiosk location. In any of these embodiments, the kiosk may include a display monitor and the kiosk enhancement may include a change to a graphical user interface displayed on the display monitor.

BRIEF DESCRIPTION OF THE DRAWINGS

The invention will now be described, by way of example only, with reference to the accompanying drawings, in which.

DETAILED DESCRIPTION OF EXEMPLARY EMBODIMENTS

Figure 1A:
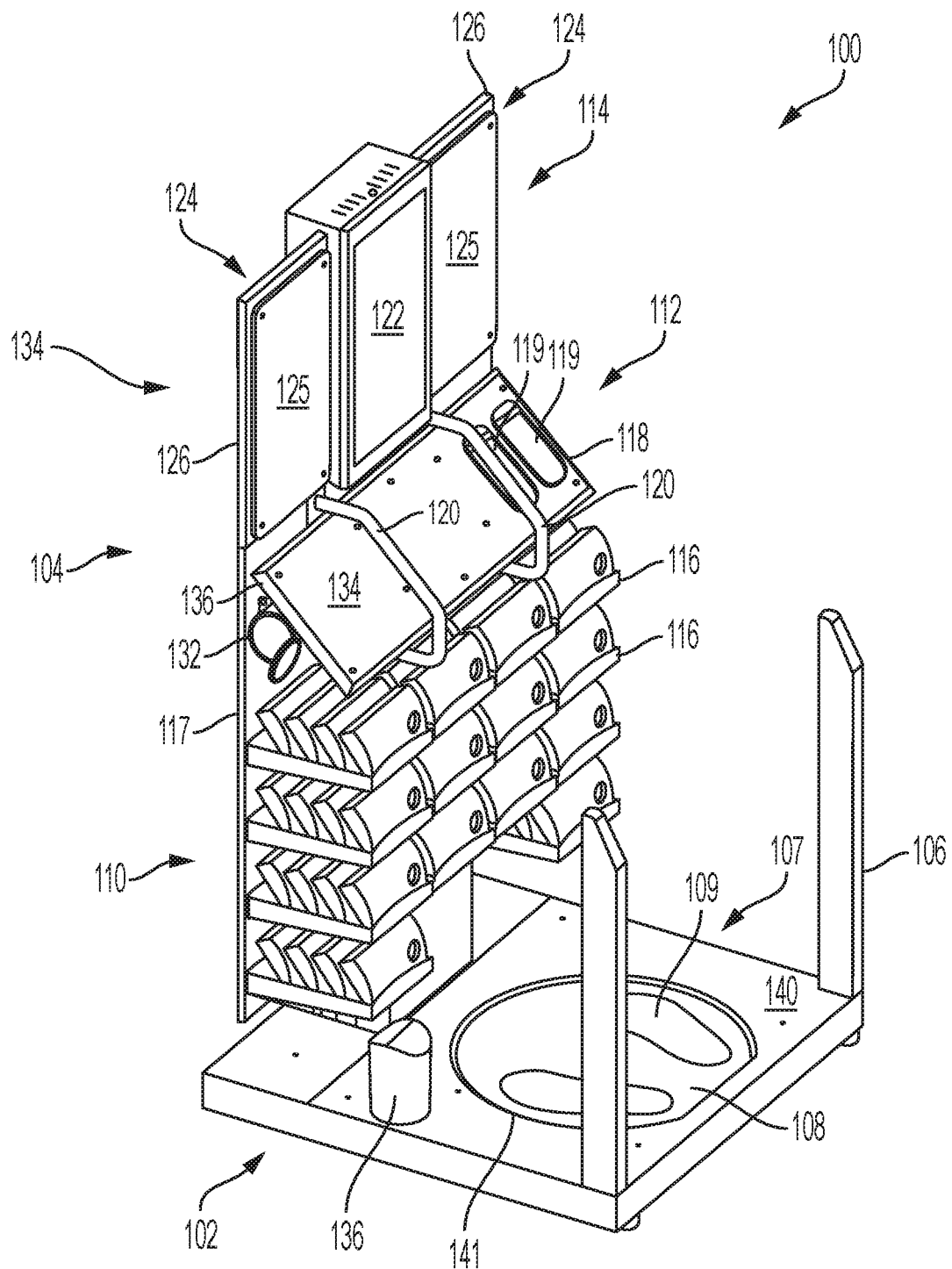
FIG. 1A is a front perspective view of a kiosk, according to some embodiments.

Described herein are systems and methods for providing product recommendations with reconfigurable kiosks that can be easily and inexpensively upgraded, updated, and enhanced over time. The kiosks may generate and collect information about a user, determine product recommendations based on the information, and provide the recommendation to the user, helping the user select from among a range of products displayed or dispensed by the kiosk. The kiosks may include one or more sensing and computing systems for generating the product recommendation and one or more displays for advertising and communicating with the user during the recommendation process. The kiosks incorporate these sensing and computing systems and displays in a reconfigurable manner so that the systems and displays can be updated. Kiosks may be updated for various reasons, including to upgrade the sensing and computing technology and to enhance the user experience through improved displays.

In some embodiments, data generated by kiosks may be used to reconfigure the kiosk. Data generated during the recommendation process may be collected by a server system and analyzed to determine kiosk enhancements that may improve the user experience and, ultimately, product sales. The analysis may result in new displays that can be easily and inexpensively incorporated into kiosks already in the field. Alternatively or additionally, sensing and/or computing technology of a kiosk can be modified based on analysis of collected data and/or a graphical user interface that guides the user through the recommendation process may be modified.

According to some embodiments, kiosks are configured for sale of orthotics such as footcare products. Footcare products may be placed inside footwear products to provide support, cushioning, to improve fit or comfort, etc. Examples of footcare products include orthotics, insoles, foot cushions, heel cups, etc. Examples of footwear products include sneakers, loafers, dress shoes, high heels, etc. A person may want to quickly and accurately determine the proper footcare or footwear product for his or her feet from an available range of products. For example, a product may need to have the proper support, size, arch support, and be able to support the person's body weight. Retailers would also want to be able to provide this service to people without having to staff a person that has specialized training and/or knowledge of all possible products, footcare or footwear, and foot types.

According to some embodiments, a kiosk measures a user's feet and determines a recommended footcare product for the user and the recommended product may be dispensed or may be selected by the person from a display on or near the kiosk. The measurements may be taken with a foot mat having pressure sensors to measure a user's feet. A processor may correlate footcare products to the user's foot measurements. In one example embodiment, the kiosk may contain a display monitor that provides instructions to the user and provides the user with an indicia of the recommended footcare product, such as a picture of the footcare product, the model number of the footcare product, a color or symbol, etc. The person may then easily locate the footcare product that will provide the best calculated fit and support for the user's needs. Alternatively, products may be dispensed from a kiosk, for example, the kiosk may be configured as a vending machine. The footcare product sold may be a pre-manufactured orthotic, and the set of candidate footcare products may be a set of different models of pre-manufactured orthotics of varying attributes, such as size, arch support levels, arch index, cushioning levels (i.e. foam density, cushioning material used, etc.), etc. The range of models provided may be chosen to address the most common conditions needing a footcare product, while coming in a range of sizes and models needed to fit and provide an appropriate support level for the vast majority of the potential user population.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a," "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

FIG. 1A illustrates footcare product dispensing kiosk 100, according to one embodiment. Kiosk 100 may generate a recommendation for a footcare product for the user based on one or more attributes of the user. The recommended product may be a pre-manufactured orthotic selected from among a set of candidate products. The set of candidate products may be a set of different models of pre-manufactured orthotics of varying attributes, such as type of orthotic product, size, arch support levels, arch index, cushioning levels (e.g., foam density, cushioning material used, etc.), etc. The range of models provided may be chosen to address common conditions needing an orthotic product, and in range of sizes and models needed to fit and provide an appropriate support level for the potential user population. The kiosk 100 is designed for reconfigurability to allow for easy and inexpensive updating of displays and recommendation system components.

Kiosk 100 includes a base 102 and a tower 104. The base 102 is locatable on a floor surface and provides a platform 107 on which a user can stand. A foot mat 108 is provided in the base 102 for measuring attributes of a user's foot as the user stands on the platform. The measurements are used to generate a recommendation for a footcare product best suited to the user. The tower 104 includes an interactive electronic display 122 for communicating with the user during the recommendation process and one or more display areas for displaying products, providing advertising, providing product information, or for any other purpose that may enhance the user's experience and/or guide a user through a recommendation process.

Tower 104 includes three primary display sections first display section 110, second display section 112, and third display section 114. However, it will be appreciated that any number of display sections organized in any suitable manner may be provided. The first display section 110 may be used for mounting a plurality of product display shelves 116. A set of candidate footcare products, such as orthotics, may be displayed on display shelves 116 to enable a user to quickly and easily obtain the footcare product recommended by the kiosk. Product may be organized in any suitable manner in the product display shelves 116. For example, footcare product may be organized by product style and by size. Display shelves 116 may be mounted on a panel 117 that can be configured to accommodate more than one arrangement of shelving. The panel 117 may be removably mounted to a central column 128 of the tower 104 allowing for the panel 117 to be easily removed and replaced with a panel of different configuration for updating the first display section 110.

Second display section 112 includes a dashboard 118 that may be used to mount various product related displays such as graphics and product samples. The dashboard 118 may be angled upward to orient mounted displays toward the eyes of a user standing on the platform 107 of the kiosk. The dashboard 118 may include one or more replaceable displays 134 that are removably mounted to a mounting panel 136 or any other suitable feature, allowing for the second display section to be updated by replacing a mounted display with an updated display. In some embodiments, the dashboard 118 includes one or more product samples 119 that may be affixed to the dashboard to enable a user to interact with the product before purchase. The dashboard 118 may be positioned at the height of a typical user's waist to provide a user easy access to the displays and/or product mounted on the dashboard 118 and to signal to the user that the display is intended to be interactive. The dashboard 118 may be mounted to the same panel 117 as the display shelves 116 or to a separate panel.

In some embodiments, one or more handles 120 may be located in the second display section 112 to aid a user in balancing on the platform, such as during foot measurement. For example, a user may grip the handles and lean forward during a measurement sequence. Handles 120 may be vertically oriented, as shown, or may be horizontally oriented and positioned above or below the dashboard 118. In some embodiments, one or more handles 120 are integrated into the dashboard. In some embodiments, the handles are mounted on panel 117 and, in other embodiments, the handles are mounted on a separate panel or directly to central column 128. In some embodiments, the handles are incorporated into one or more brackets that are mounted to the central column 128 or a panel (such as panel 117) and the dashboard 118 is mounted on a portion of the brackets.

The third display section 114 includes one or more interactive electronic displays 122. The interactive display 122 may include a display monitor for displaying a graphical user interface. The interactive display 122 may provide on-screen step-by-step instructions that guide a user through the product recommendation process and may provide an indication of the recommendation to the user on the display 122 at the conclusion of the process. In some embodiments, the interactive display 122 is a touch screen monitor, providing user input capability. The interactive display 122 may be located at a suitable location relative to a user standing on the platform of 107 of the kiosk 100, such as at or near eye level of an average user.

One or more updatable displays 124 may also be provided in the third display section 114. In the embodiment illustrated in FIG. 1A, an updatable display 124 is provided on the right and left sides of the interactive electronic display 122. Each updatable display 124 may include a mounting portion 126 and a display portion 125. The display portion 125 may be a panel or other substrate with printed graphics or other medium that can be mounted to the mounting portion 126, such as on bosses or standoffs. The mounting portion 126 may be a panel, a bracket, or any other suitable support for the display portion. An updatable display 124 can be updated by replacing the display portion 125 with a display portion having different graphics or other form of display without replacing or modifying the mounting portion 126. In some embodiments, the mounting portion 126 may also be replaced to accommodate a display portion of a different size or shape. The mounting portion 126 may be affixed to the central column 128, for example, with brackets or any other suitable mounting means.

Kiosk 100 may be easily and inexpensively updated by simply replacing one or more updatable displays 124 or one or more display portions 125 of the updatable displays 124. In some embodiments, one or more of the updatable displays 124 includes an electronic display, which can allow for updating of the kiosk via software updates for the software controlling the graphic display by the electronic display. Although illustrated in FIG. 1A as rectangular, the updatable displays 124 can be any suitable shape and any suitable size. In some embodiments, one or more updatable display 124 is sized to accommodate the same size of monitor as provided in the interactive electronic display 122.

Figure 1B:
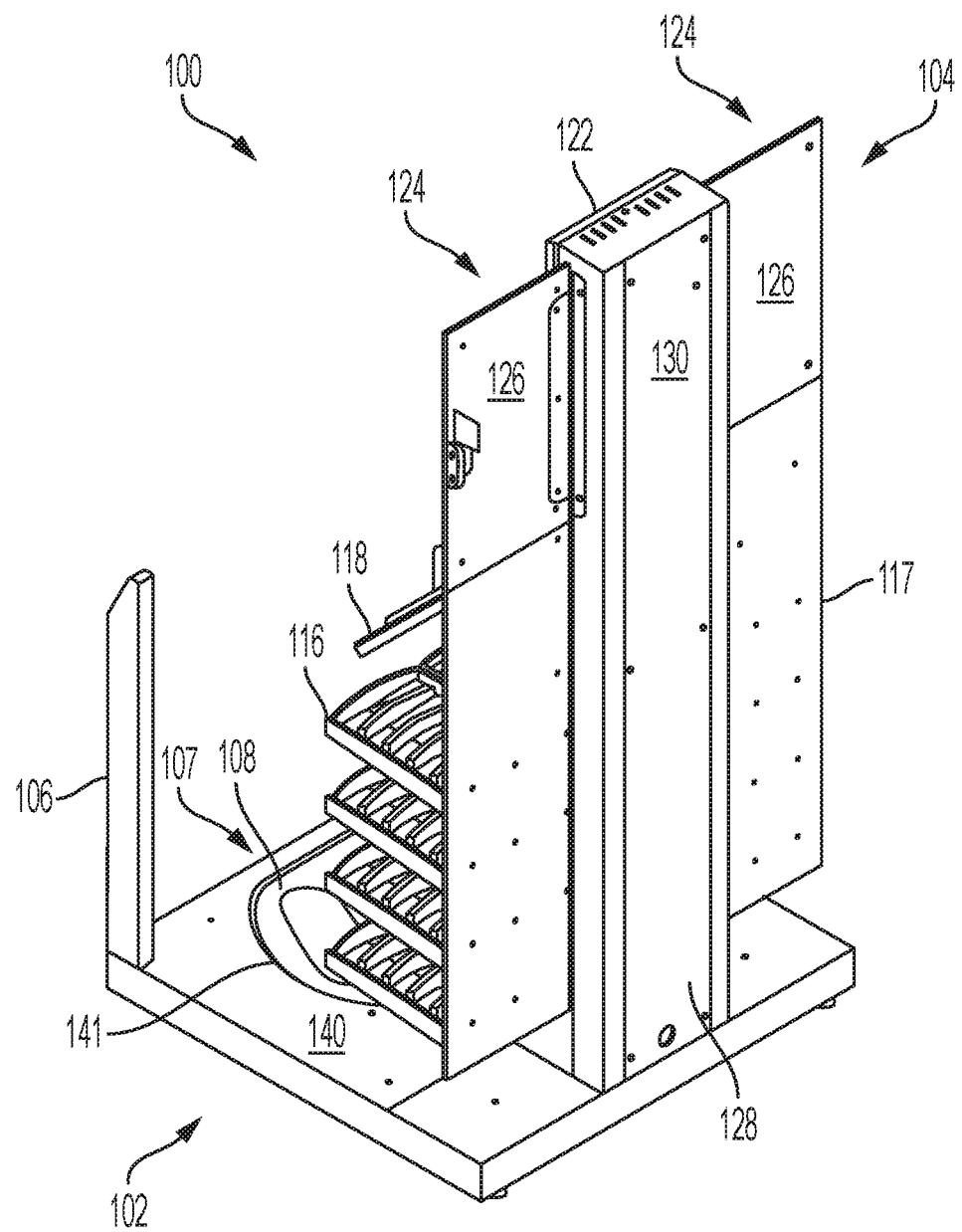
FIG. 1B is a rear perspective view of the kiosk of FIG. 1A.

FIG. 1B is a rear view of kiosk 100, according to some embodiments. As described above, the tower 104 includes a central column 128 that provides mounting locations for the display sections. For example, in the illustrated embodiment, the mounting panel 117 of the first display section 110 mounts to a forward facing side of the central column 128 and the mounting portions 126 of the updatable displays 124 are mounted via brackets to the sides of the central column 128.

The central column 128 may serve as a housing for electronics, such as computing and communications equipment for generating product recommendations. Central column 128 may form a raceway for routing wiring such as power cords and sensor mat wiring from the base to computing components in the central column 128, such as to an interactive display 122. A cover panel 130 may be provided on the rear of the central column 128 and may be removable to provide easy access to the wiring and/or electronics housed within. In some embodiments, a base of the central column 128 may house electronics such as computing equipment. In some embodiments, electronics housed in the base may be accessed by removing the cover panel 130. In some embodiments, a removable cover panel is provided on a front of the base of the column (facing the user) for accessing electronics housed in the base. Housing at least some of the electronics in the base of the central column 128 may be beneficial in reducing the amount of space required for electronics housed in other portions of the kiosk such as behind the display 122, as discussed further below.

Figure 1C:
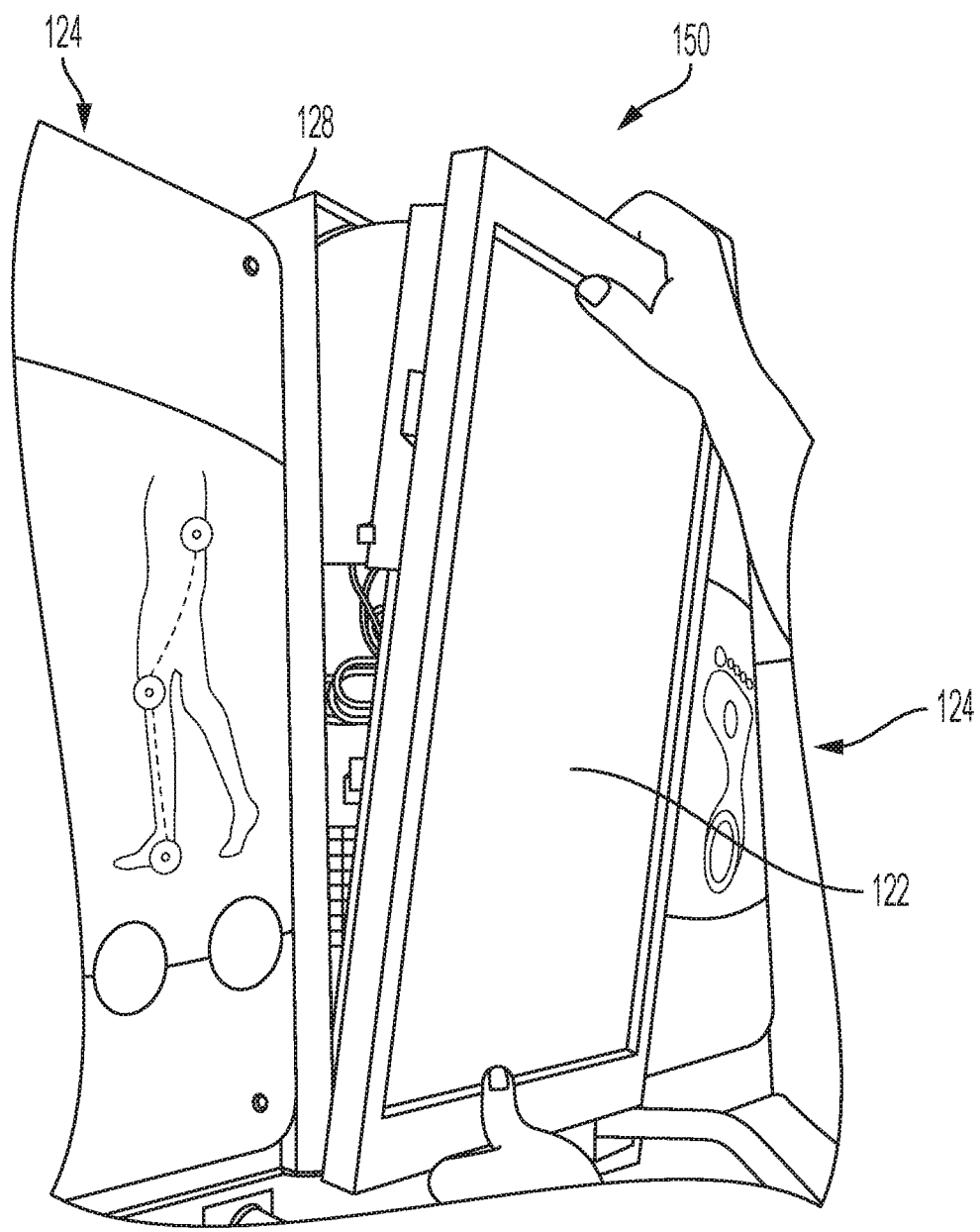
FIG. 1C illustrates the removal of an interactive display, according to some embodiments.

FIG. 1C illustrates the mounting of interactive display 122 to the central column 128, according to one embodiment. The interactive display 122 may be received in an opening in the front side of the central column 128. In some embodiments, the interactive display is configured as a modular unit with computing hardware mounted on a rear side and a display screen mounted on the front side.

Figure 1D:
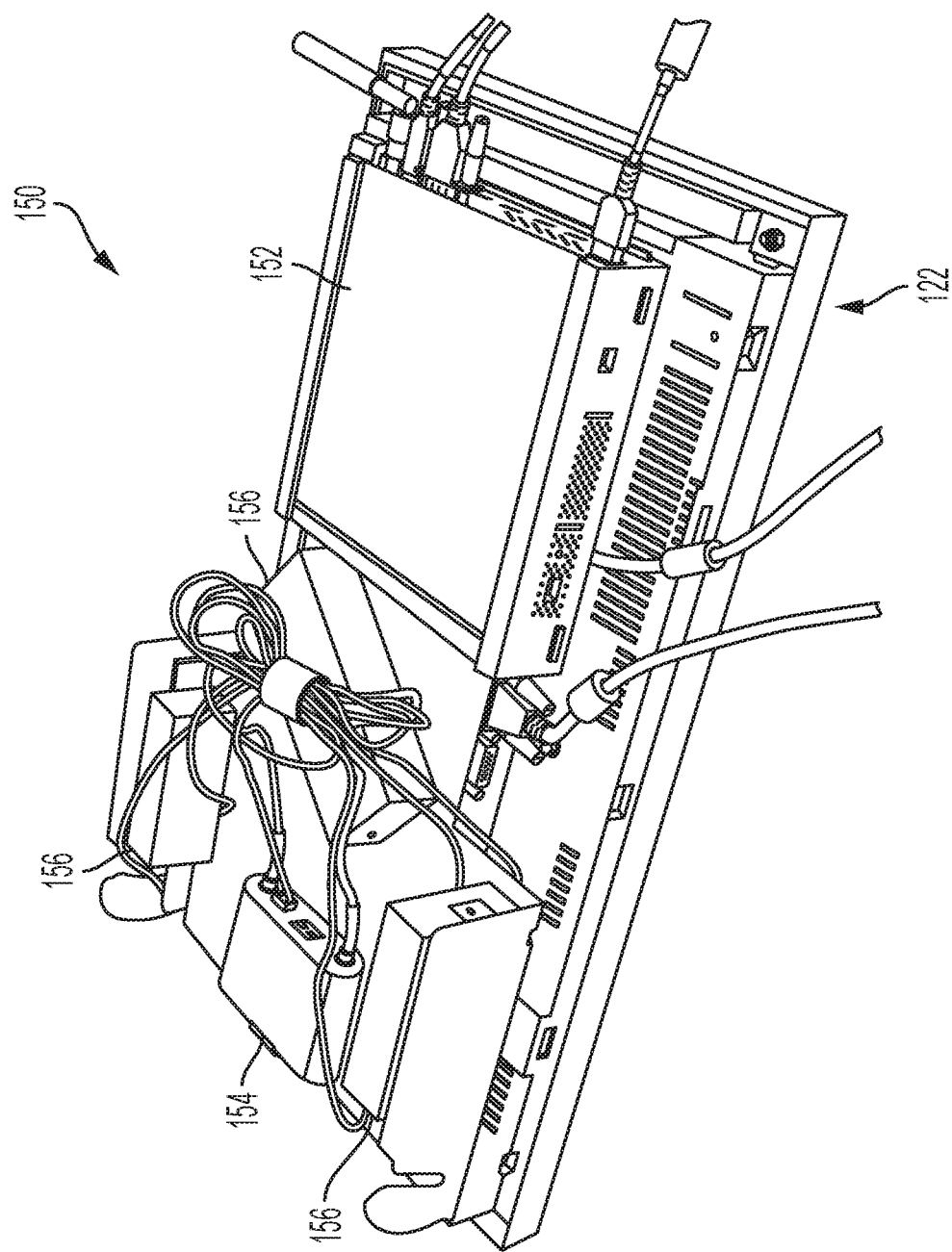
FIG. 1D is a rear view of an interactive display module illustrating the mounting of electronic components, according to some embodiments.

FIG. 1D is a rear view of an exemplary modular unit 150 that incorporates an exemplary interactive display 122 with computing components for the kiosk 100. The interactive display 122 is provided on a front side of the modular unit 150 and computing components, such as a computer 152, modem 154, and power packs 156, are provided on a rear side. In some embodiments, incorporating computing and communication hardware right behind the display screen as a modular unit, rather than, for example, in lower portions of the central column or in the base of the kiosk, more space along the tower 104 is made available for displays and/or product shelving. In other embodiments, including at least some computing and communication hardware in the base of the central column 128 provides more space in the interactive display area that can be utilized, for example, for more product-related display and/or a larger monitor. Wiring such as power supply cabling for providing power to the computing system of the kiosk and wiring from one or more sensors in the base 102 of the kiosk may be routed to the computing components in the modular unit 150 through central column 128.

Figure 1E:
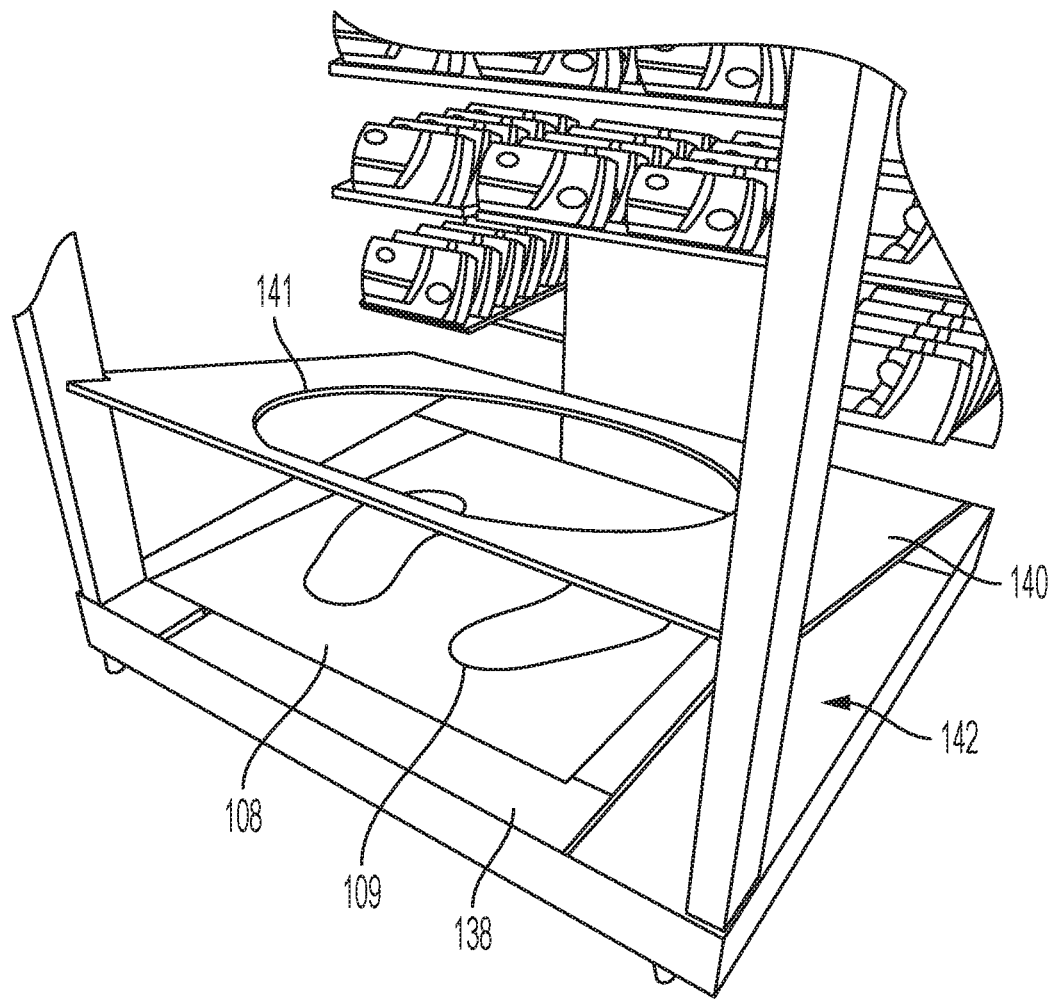
FIG. 1E illustrates the integration of a foot mat in the base of a kiosk, according to some embodiments.

The base 102 of the kiosk 100 may also include reconfigurable features that can accommodate updating of the kiosk 100 over time. According to some embodiments, base 102 houses a foot mat 108, which may include one or more sensors for measuring attributes of a user's foot. As shown in FIG. 1E, the base may include a recess 138 in which the foot mat 108 is positioned. A top plate 140 may be placed above the foot mat 108 and removably fastened to the base 102. Top plate 140 may include a cutout 141 configured to leave the sensor area of the foot mat 108 uncovered. In some embodiments, the foot mat 108 includes one or more foot placement indicators 109 (e.g., foot prints) for indicating to a user where to stand for measurement.

Located within the recess 138 is a spacer system 142 that is configured to position the foot mat 108 within the base 102. The spacer system 142 may be reconfigured to accommodate foot mats of different sizes and shapes, allowing the same kiosk 100 to be used with multiple foot mat designs. The spacer system 142 includes one or more spacers sized to fit within the side walls of the base 102 and sized to fit the configuration of the foot mat 108. Different sized and shaped spacers can be used to accommodate different size foot mats so that the same kiosk can incorporate foot mat of different configurations. The spacer system may locate the foot mat 108 laterally side-to-side and/or front-to-back within the recess 138 in the base 102, which may ensure that the sensor portion of the foot mat 108 is entirely or at least partially within the cutout 141 of the top plate 140 or to ensure that the foot placement indicators 109 are located within the cutout 141. In some embodiments, one or more spacers may be included beneath the foot mat 108 to control the depth positioning of the foot mat 108 within the recess 138 allowing for foot mats of different thickness.

Figure 1F:
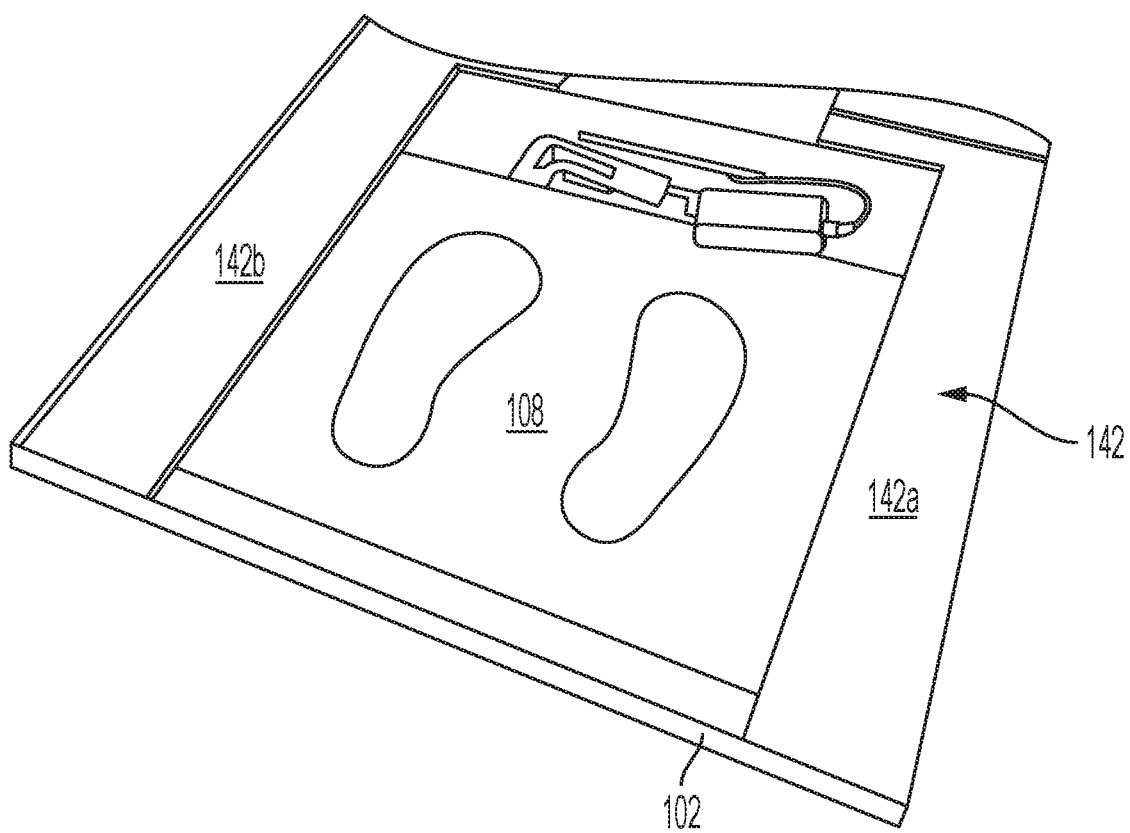
FIG. 1F illustrates the base of a kiosk with the cover plate removed showing a foot mat and spacer system, according to some embodiments.

FIG. 1F illustrates an exemplary spacer system 142 and foot mat 108 positioned within base 102. In the illustrated embodiment, the spacer system 142 includes two L-shaped spacers 142a,b that extend along the sides of a recess in the base 102 and register against the four sides of the recess of the base 102. In the illustrated embodiments, the spacers position the foot mat 108 centrally within the recess of the base 102. It will be appreciated that a spacer system can include any suitable number, shape, and dimensions of spacers to accommodate various foot mat configurations. For example, in some embodiments a spacer may be configured as a single piece with a cutout sized for a foot mat. Spacers may be formed of any suitable material or combination of materials, including any suitable plastics and metals. In some embodiments, spacers are made of wood or a wood product such as particle board or fiber board. Spacers may be positioned in the base 102 with or without fasteners. In some embodiments, one or more spacers are configured to register to the sides of the recess 138 such that the spacers cannot move laterally, allowing for the spacers to be positioned without fasteners. This may increase the ease with which the spacers can be replaced to accommodate different foot mat configurations.

With the spacer system 142 and foot mat 108 in place, the top plate 140 is placed on top of the foot mat and spacer system. The cutout 141 in the top plate 140 may enable the user to stand directly on the sensor area of the foot mat 108. The cutout can be configured in any suitable way to accommodate the sensor area of a particular foot mat configuration. In some embodiments, one or more spacers of the spacer system 142 provides sufficient support for the top plate 140 and/or foot mat 108 to accommodate a user standing on the tope plate 142. Foot mats of varying configuration can be accommodated in the kiosk 100 simply by replacing one or more spacers of the spacer system and/or the top plate.

The foot mat 108 may include one or more pressure sensors for measuring pressure applied by the user's feet. Examples of foot mats that may be used according to some embodiments are provided in U.S. Pat. No. 8,117,922, "Footcare Product Dispensing Kiosk," the entire contents of which is hereby incorporated by reference in its entirety. The foot mat 108 may have an outline of feet or a depressed area for the feet to advantageously constrict a position of the user so that the measurement data is accurate. The foot mat 108 may include an array of pressure sensors made from pressure sensitive conductive inks, such as sensors from Tekscan, Inc. (307 West First Street, South Boston, Mass.

02127-1309, USA), and/or sensors described in U.S. Pat. Nos. 5,989,700 and 6,964,205. Other measurement technologies may also be employed, such as force plates, piezoelectric sensors, digital air pressure sensors, optical measurements, gauges, thermal sensors, etc.

The foot mat 108 may be arranged to obtain pressure measurements at different points of a user's foot. For example, the pressure sensors may be arranged as a 2-D grid or a 3-D grid of multiple sensor layers that may provide the measurements needed to provide an accurate pressure map of the foot. The sensor area of the foot mat 108 may vary depending on the target population. For example, an example embodiment of the kiosk 100 may contain pressure pads underlying the feet that are capable of measuring children to adults, and the pads may be large enough to capture the foot area of an adult.

Kiosks, according to various embodiments, may incorporate any number of sensors for measuring aspects of a user. For example, an imaging sensor may be included for imaging a user's feet, ankles, knees, whole body, face, or any other attribute of the user. Sensors may be located in the base 102 or in the tower 104. For example, an imaging sensor may be located in a lower portion of the tower 104 for imaging aspects of the user's lower leg and/or feet or may be located in an upper portion of the tower to image the whole body or the face.

Kiosk 100 may include other features such as one or more guide pillars 106 that may extend from the base 102 for guiding a user onto the platform 107. In some embodiments, guide pillars 106 may be configured as handles that a user can grasp for support while on the platform.

In some embodiments, a consumables dispenser 132 that may be included to provide users with, for example, sanitary wipes for wiping down surfaces of the kiosk or disposable sock that a user may wear when standing on the platform. The consumables dispenser 132 may be located behind the dashboard 118, utilizing space provided by the angled positioning of the dashboard 118. However, it should be appreciated that the consumables dispenser 132 may be located in any suitable location on the kiosk 100. In some embodiments, a mount is provided behind the dashboard for an off-the-shelf consumable dispenser, such as a sanitary wipe dispenser, enabling easy refilling. In some embodiments, a trashcan 136 may be provided, for example, on the base 102, for disposing consumables.

Footcare Product Recommendation System

Figure 2:
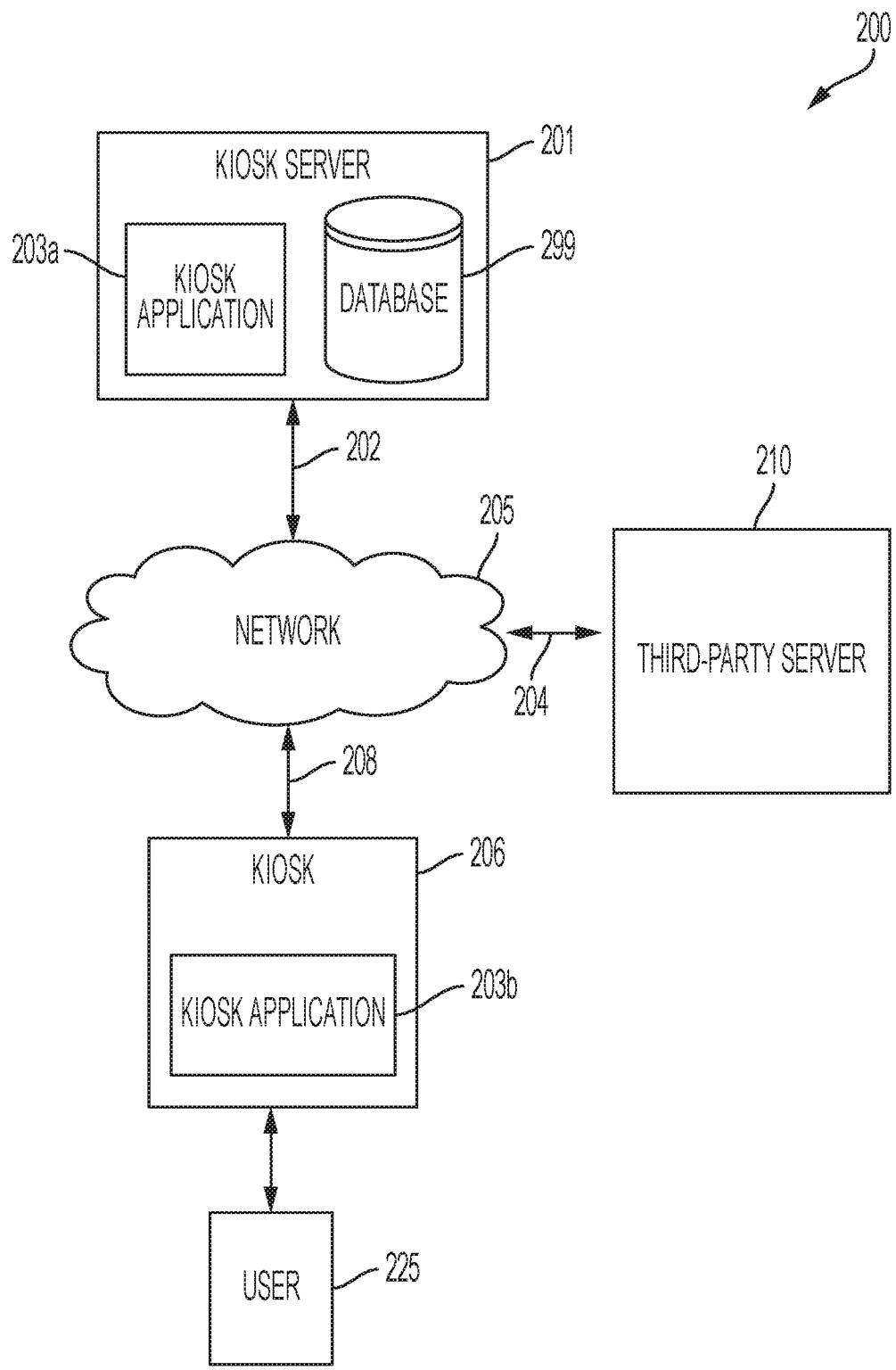
FIG. 2 illustrates a block diagram of an example system for generating a footcare product recommendation, according to some embodiments.

FIG. 2 illustrates a block diagram of an example system 200 that generates product recommendations for users. The illustrated system 200 includes a kiosk server 201, a kiosk 206, a third-party server 210, and a network 205.

The kiosk server 201 may include a processor, a memory, and network communication capabilities. In some embodiments, the server 201 is a hardware server. The server 201 is communicatively coupled to the network 205 via signal line 202. Signal line 202 may be a wired connection, such as Ethernet, coaxial cable, fiber-optic cable, etc., or a wireless connection, such as Wi-Fi, Bluetooth, cellular, or others wireless technology.

In some embodiments, the kiosk server 201 communicates with the kiosk 206 via the network 205. The kiosk server 201 may include one or ore kiosk server applications 203a and a database 299. The kiosk server application 203a may communicate with one or more kiosk applications 203b running on the kiosk 206. For example, the kiosk server application 203a may receive product recommendation related information and/or kiosk related information from the kiosk application 203b. The kiosk server application 203a may also transmit information to the kiosk application 203b running on the kiosk 206. For example, the kiosk server application 203a may push updates to the kiosk application 203b or command a restart of the kiosk and/or kiosk application 203b.

The one or more kiosk applications 203b may be code and routines configured to generate a product recommendation for a user 225. In some embodiments, the kiosk application 203b may be implemented using hardware including a field-programmable gate array (FPGA) or an application-specific integrated circuit (ASIC). In some embodiments, the kiosk application 203b may be implemented using a combination of hardware and software. In the illustrated embodiment, the kiosk 206 is coupled to the network 205 via signal line 208. Signal line 208 may be a wired connection, such as Ethernet, coaxial cable, fiber-optic cable, etc., or a wireless connection, such as Wi-Fi, Bluetooth, cellular, or other wireless technology. While FIG. 1 illustrates one kiosk 100 and one user 225, embodiments may include any number of kiosks 206 providing recommendation to any number of users 225.

The third-party server 210 may include a processor, a memory, and network communication capabilities. The third-party server 210 may be configured to send data to and from the kiosk 206 and/or the kiosk server 201. For example, the third-party server 210 may include an application configured to determine a stock of footcare products in one or more physical stores or other kiosks 206. In another example, the third-party server 210 may include an application configured to order a custom-made footcare product for the user 225. The third-party server 210 may communicate with the network 205 via signal line 204.

In some embodiments, a third-party server 210 provides a customer relationship management (CRM) platform for analyzing data related to kiosks and the products recommended by the kiosks. Data gathered from kiosks 206 may be provided to a CRM platform for analysis, either directly from each kiosk 206 or via kiosk server 201. CRM platform may gather and compile data such as product sales information from, for example, retail stores or the product manufacturer. The CRM platform may apply techniques such as data mining, correlation, and pattern recognition to analyze the data for determining possible kiosk enhancements that may improve the customer experience and result in increased sales.

In the illustrated implementation, components of the system 200 may be communicatively coupled via a network 205. The network 205 may include a local area network (LAN), a wide area network (WAN) (e.g., the Internet), and/or other interconnected data paths across which multiple devices may communicate. In some embodiments, the network 205 may be a peer-to-peer network. The network 205 may also be coupled to or include portions of a telecommunications network for sending data in a variety of different communication protocols, in some embodiments, the network 205 includes Bluetooth® communication networks or a cellular communications network for sending and receiving data including via short messaging service (SMS), multimedia messaging service (MMS), hypertext transfer protocol (HTTP), direct data connection, wireless application protocol (WAP), email, etc. Although FIG. 2 illustrates one network 205 coupled to the kiosk 206, the kiosk server 201, and the third-party server 210, in practice one or more networks 205 may be coupled to these entities.

In some embodiments, the footcare product recommendation system 200 is configured to provide a custom footcare product to a user based on measurements of the user's foot that are collected at a kiosk, such as kiosk 100. Information about a user that is collected by a kiosk may be provided to a custom footcare product platform (e.g., running on a server in communication with the kiosk) that is configured to generate a custom footcare product design that is specific to the user and designed based on the information about the user collected by the kiosk, including user foot mapping, user biographics, and/or any other information generated or collected by the kiosk. The custom footcare product design may then be manufactured specifically for the user and delivered to the user. For example, the custom footcare product may be manufactured in a custom footcare product manufacturing facility and then shipped from the facility to the user's home based on user address information collected from the user at the kiosk.

In some embodiments, some or all of the custom footcare product may be 3D printed based on foot mapping measurements taken by the kiosk. Other user information such as gender, age, and weight may be used by the custom footcare product platform to design the custom footcare product. In some embodiments, the custom footcare product may be an assembly of pre-made components. For example, a custom footcare product for a user may be assembled from a pre-formed base that may be selected based on one or more of the user's attributes, from a pre-formed arch shell that may be selected based on one or more of the user's attributes, and/or from a pre-formed heel cup that may be selected based on one or more of the user's attributes. Thus, though some or all of the individual components may not be custom, the combination of the selected component results in a custom footcare product that is tailored to the user.

Example Computing Device

Figure 3:
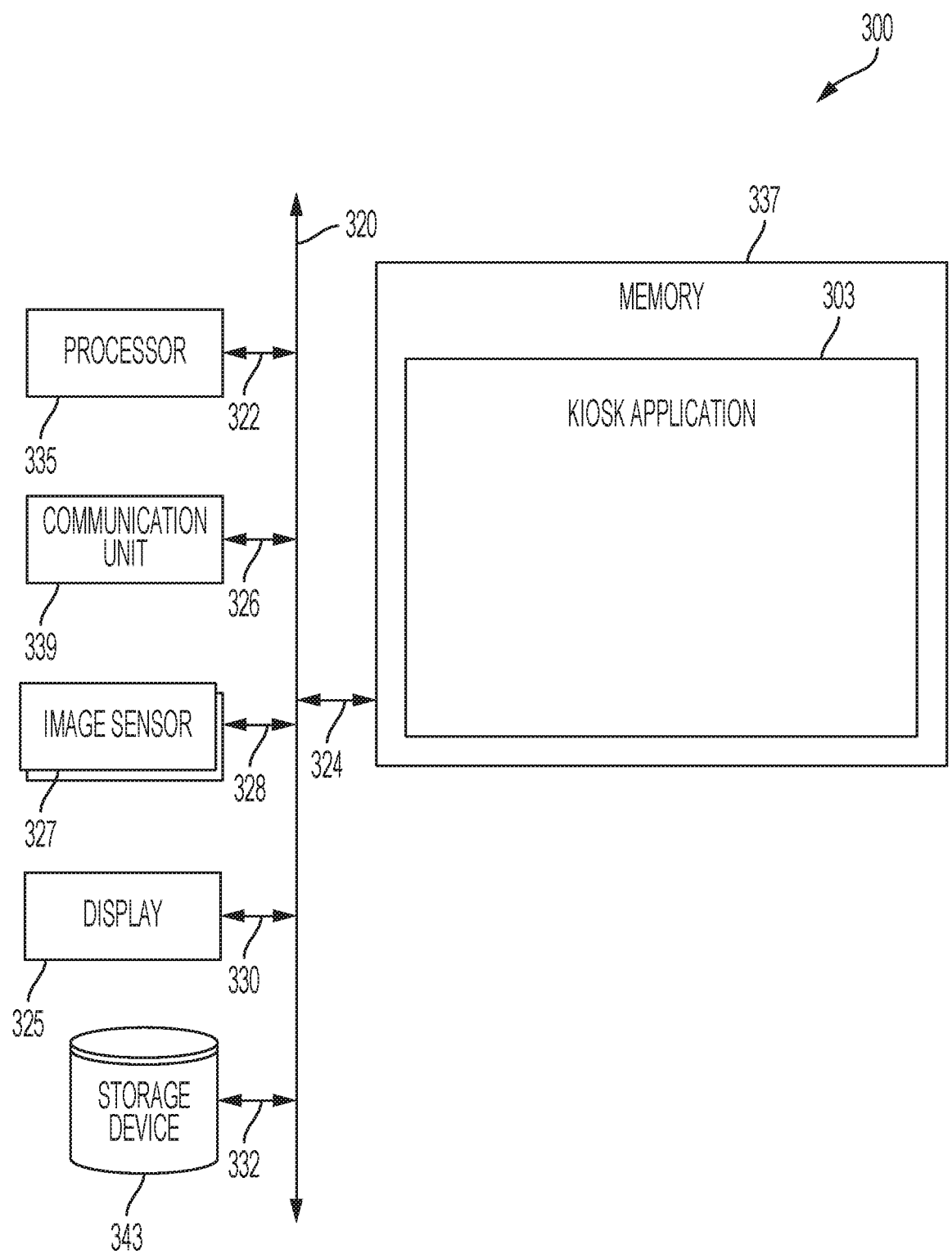
FIG. 3 illustrates a block diagram of an example computing apparatus for generating an orthotic product recommendation, according to some embodiments.

FIG. 3 illustrates a block diagram of an example computing apparatus 300 for generating a footcare product recommendation. The computing apparatus 300 may be incorporated in a kiosk such as kiosk 100 and kiosk 206. The computing apparatus 300 may include a processor 335, a memory 337, a communication unit 339, one or more sensors 327, a display monitor 325, and a storage device 343. The components of the computing apparatus 300 may be communicatively coupled by a bus 320.

The processor 335 may include an arithmetic logic unit, a microprocessor, a general purpose controller or some other processor array to perform computations and provide instructions to a display device. Processor 335 processes data and may include various computing architectures including a complex instruction set computer (CISC) architecture, a reduced instruction set computer (RISC) architecture, or an architecture implementing a combination of instruction sets. Although FIG. 3 includes a single processor 335, multiple processors 235 may be included. Other processors, operating systems, sensors, displays and physical configurations may be part of the computing apparatus 300. The processor 335 is coupled to the bus 320 for communication with the other components via signal line 322.

The memory 337 stores instructions that may be executed by the processor 335 and/or data. The instructions may include code for performing the techniques described herein. The memory 337 may be a dynamic random access memory (DRAM) device, a static RAM, or some other memory device. In some embodiments, the memory 337 also includes a nonvolatile memory, such as a (SRAM) device or flash memory, or similar permanent storage device and media including a hard disk drive, a solid state drive, a flash memory device, or some other mass storage device for storing information on a more permanent basis. The memory 337 includes code and routines configured to execute the kiosk application 303. The memory 337 is coupled to the bus 320 for communication with the other components via signal line 324.

The communication unit 339 transmits and receives data to and from the network. In some embodiments, the communication unit 339 includes a port for direct physical connection to a network such as network 205 or to another communication channel. In some embodiments, the communication unit 339 includes a wireless transceiver for connecting to the network, using one or more wireless communication methods, including Wi-Fi, Bluetooth, cellular, or other wireless technology. The communication unit 339 is coupled to the bus 320 for communication with the other components via signal line 326.

In some embodiments, the communication unit 339 includes a cellular communications transceiver for sending and receiving data over a cellular communications network including via short messaging service (SMS), multimedia messaging service (MMS), hypertext transfer protocol (HTTP), direct data connection, WAP, e-mail or another suitable type of electronic communication. In some embodiments, the communication unit 339 includes a wired port and a wireless transceiver. The communication unit 339 may provide other conventional connections to the network for distribution of files and/or media objects using standard network protocols including, but not limited to, UDP, TCP/IP, HTTP, SMTP, SPICY, QUIC, etc.

The one or more sensors 327 may include pressure sensors incorporated in a foot mat of a kiosk for measuring the contours of a user's foot, such as foot mat 108 of kiosk 100. Any other suitable sensors may be included, such as imaging sensors, heartrate monitors, weight scales, and temperature sensors. The sensors 327 are coupled to the bus 320 via signal line 328.

The display monitor 325 may include hardware configured to display graphical data. For example, the display monitor 325 may render graphics to display a user interface that is configured to display a product recommendation. The display monitor 325 is coupled to the bus 320 for communication with the other components via signal line 330.

Other hardware components that provide information to a user may be included as part of the computing apparatus 300. For example, the computing apparatus 300 may include a speaker for audio interfaces or other types of non-display output devices. The computing apparatus may include any suitable input feature, such as a touchscreen monitor, voice recognition, a mouse, a keyboard, or a remote control.

The storage device 343 may be a non-transitory computer-readable storage medium that stores data that provides the functionality described herein. The storage device 343 may be a DRAM device, a SRAM device, flash memory or some other memory device. In some embodiments, the storage device 343 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a permanent basis. The storage device 343 is coupled to the bus 320 for communication with the other components via signal line 332.

The kiosk application 303 may be configured to provide information to and receive information from a user, such as through a touchscreen of the kiosk. The kiosk application 303 can be stored in the memory 337 of the computing apparatus 300 and can be accessible and executable by the processor 335. The kiosk application 303 may generate a user interface to interact with a user, such as for guiding a user through a recommendation process and/or displaying the recommendation to the user. Kiosk application 303 may receive scan data from one or more sensors 327 and may generate a real-time image or video of the user to assist the user in proposer positioning on or relative to the kiosk.

Kiosk application 303 generates a product recommendation based on data received from the one or more sensors 327. For example, kiosk application 303 may generate footcare product recommendations using methods described in described in U.S. Pat. No. 8,117,922, "Footcare Product Dispensing Kiosk." Kiosk application 303 may store product recommendation information in storage device 343 and may periodically transmit the information to a server system, such as kiosk server 201 or third-party server 210 of system 200. Product recommendation information that may be stored and transmitted may include user interface activity logs such as step-on logs (e.g., logs of detections of users stepping on the platform of the kiosk), pre-scan logs for information generated by the kiosk before initiation a scan of the user, foot scans, scan analyses, product recommendation logs, user interface page navigations, or any other data that is generated to the process for providing a user recommendation.

Kiosk application 303 may also store and transmit information related to the kiosk, such as restart logs, heartbeat logs, application open/close logs, hardware status logs (for example pressure mat diagnostics logs), or any other kiosk related data. The kiosk application 303 may transmit kiosk identifiers and/or kiosk location information. Kiosk location information can include geographic location information, information about the environment where the kiosk is located (such as a store identifier), or any other information related to where the kiosk is located. As described below, any of this information may be used to generate updates for a reconfigurable kiosk, such as kiosk 100.

Kiosk Updating Method

Figure 4:
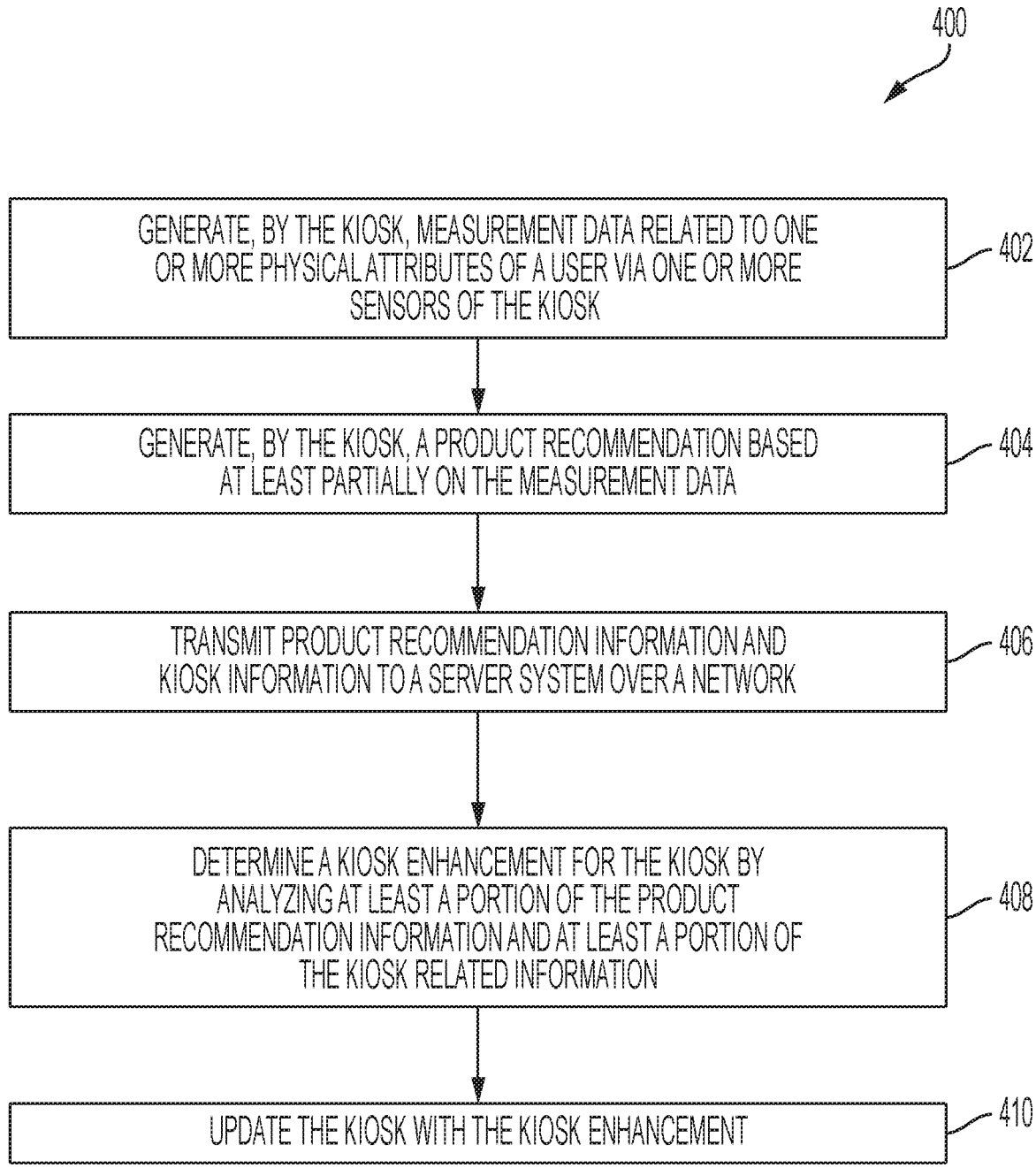
FIG. 4 is a flowchart illustrating an exemplary method for updating a product recommendation kiosk, according to some embodiments.

FIG. 4 is a flow chart illustrating a method 400 for updating a kiosk based on usage of the kiosk. At step 402 the kiosk generates measurement data related to one or more physical attributes of a user via one or more sensors in the kiosk. For example, a foot mat located in the based on the kiosk may include one or more pressure sensors for measuring the pressure distribution over a user's foot or feet as the user stands on the foot mat. One or more kiosk applications, such as kiosk application 303 running on processor 335 of computing apparatus 300, may direct the measurement generation process and may store measurement data generated based on the sensor measurements. For example, a pressure map of the user's feet may be generated through a scan process guided by a graphical user interface displayed on a display monitor (e.g., of interactive display 122 of kiosk 100) and the pressure map may be stored in storage device 343 of the kiosk. Measurement data may be generated in any suitable way with any suitable combination of sensors. For example, measurement data may be generated as described in U.S. Pat. No. 8,117,922.

At step 404, a product recommendation is generated by the kiosk based at least partially on the measurement data. For example, a biomechanical data estimate of the foot may be calculated using the pressure measurements and used to generate a product recommendation. The biomechanical data may be compared with values from a decision matrix of footcare products and classified subgroups for recommending a footcare product based on a user's classified subgroups. A classified subgroup may include the weight of the person, the band of the person (i.e. a band based on a person's foot length), a person's arch index, etc. For example, a footcare product recommendation may be generated as described in U.S. Pat. No. 8,117,922.

At step 406, product recommendation information and kiosk information is transmitted to a server system over a network. For example, kiosk application 203b of system 200 may direct transmission of product recommendation information and kiosk information to kiosk server 201 and/or third-party server 210. This information may be transmitted periodically at regular or irregular intervals. For example, information may be transmitted after completion of each product recommendation process or may be transmitted on an hourly, daily, or weekly basis. Information may be transmitted during a product recommendation process. In some embodiments, transmitting information, such as user attribute measurements, during a product recommendation process may enable a server based kiosk application to participate in the recommendation process. Information transfer may be initiated by the kiosk or by a server application or by both depending on the circumstances. For example, a kiosk may be configured to transmit information such as product recommendation information after the completion of a product recommendation process and a server may be configured to request transmission of kiosk information at regular intervals.

Product recommendation information that may be stored and transmitted may include user interface activity logs such as step-on logs (e.g., logs of detections of users stepping on the platform of the kiosk), pre-scan logs for information generated by the kiosk before initiation a scan of the user, foot scans or other user attribute scans, scan analyses, product recommendation logs, user interface page navigations, or any other data that is generated to the process for providing a user recommendation. Product recommendation information may include user information such as user height, user weight, user age, user gender, time of recommendation generation, user contact information, or any other user-specific information generated or collected by a kiosk during a recommendation process.

In some embodiments, measurements generated by a kiosk may be used by a kiosk application to estimate user-specific attributes such as gender that may be included in transmitted product recommendation information. In some embodiments, users may be prompted to input user-specific information. The user may be prompted, for example, by a user interface of the kiosk, to enter height, gender, and/or age to assist in selecting a recommended product for the user. In some embodiments, the user may be offered a rebate that requires the user to input contact information such as email addresses. User identification information such as names, addresses, phone numbers, and/or email addresses may be anonymized by the kiosk before storage on the kiosk and/or before transmission to the server to protect a user's identity. For example, user identification may be reduced to a hash value or other anonymous form.

Kiosk information may include information that is independent of user interaction and may include information related to kiosk restarts, kiosk heartbeats, application opens/closes, hardware status such as sensor diagnostics and/or calibration, or any other kiosk related data. Kiosk information may include kiosk identifiers and/or kiosk location information, such as geographic location information and any other information related to where the kiosk is located.

At step 408, a kiosk enhancement for the kiosk may be determined by analyzing at least a portion of the product recommendation information and at least a portion of the kiosk related information. As a simple example for purposes of illustrating step 408, analysis of the data received from the kiosk may indicate that a particular kiosk is used mostly by women and an enhancement for the kiosk may be determined to be advertising targeting women. An enhancement may be an update to a physical feature of the kiosk, such as a new advertising decal for replacing existing decals on the kiosk. An enhancement could be a modification to one or more graphical user interfaces displayed on a monitor of the kiosk.

Enhancements may be determined using information received by the server from sources other than a kiosk. For example, product sales information for the product displayed at the kiosk may be received from a store where the kiosk is installed. Information received from other kiosks may also be used to determine an enhancement for a particular kiosk or set of kiosks.

According to some embodiments, kiosk enhancements are determined at least partially by providing product recommendation information and/or kiosk information to a CRM platform and receiving results of an analysis of at least some of the date from the CRM platform. For example, an CRM analysis may indicate the periods in the day and/or week during which a kiosk is most used or least used and an enhancement may be determined based at least partially on this information. A CRM platform may be operating on a kiosk management server, such as server 201 of system 200, on a third-party server such as third-party server 210 of system 200, or a combination thereof.

At step 410, the kiosk is updated with the kiosk enhancement determined at step 408. For example, a user interface displayed on a display monitor of the kiosk may be modified to include advertising targeting users that are determined during the analysis of the information received from the kiosk to be more likely to use the kiosk. One or more physical displays (i.e., non-electronic displays) on the kiosk may be replaced with an enhanced display. For example, analysis of information received from the kiosk may indicate that users are struggling through one or more aspects of the recommendation process and an updated instruction decal may be added to the kiosk.

The reconfigurability of a kiosk, such as kiosk 100, allows for easy and inexpensive implementation of enhancements. For example, the display portions 125 of the updatable displays 124, may be replaced with updated displays or an electronic display may replace a non-electronic display. Product shelving may be reorganized to incorporate more of a given product, for example, based on sales data and/or user information. An installed foot mat 108 may be replaced with an enhanced sensor mat of the same or different size and/or shape to generate enhanced foot scans as determined by the analysis of foot scans received from one or more kiosks. One or more computing components installed in the modular unit 150 may be easily swapped out to improve kiosk performance, based for example, on an analysis of the number of system restarts and/or network connection drops.

It will be appreciated that kiosk enhancements may be developed based on analysis of any combination of data generated by the kiosk and data collected from sources other than kiosk to better tailor a particular kiosk or set of kiosks to users. The reconfigurable design of kiosks according to the principles described above allow for a greater number and kind of enhancements than many existing kiosks and allow for easy and inexpensive updating of the kiosks over time with enhancements.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A kiosk for providing footcare product recommendations, the kiosk comprising:
    a base;
    a foot mat in a recess of the base;
    a spacer system in the recess of the base for positioning the foot mat, the spacer system positioned between and registered against at least one side wall of the base and at least one side wall of the foot mat; and
    a removable cover plate placed on top of the foot mat and the spacer system, the cover plate comprising an opening leaving at least a portion of the foot mat uncovered;
    wherein the foot mat comprises foot shaped indicators for guiding a user where to stand on the foot mat, wherein the opening in the cover plate is large enough to leave the indicators uncovered, and wherein the spacer system is comprised of at least two L-shaped spacers configured to position the indicators beneath the opening in the cover plate.

2. The kiosk of claim 1, wherein the foot mat is configured to obtain pressure measurements at different points of a foot of a user.

3. The kiosk of claim 1, wherein the foot mat comprises a sensor area for measuring a foot of a user.

4. The kiosk of claim 1, wherein the spacer system is sized to fit within side walls of the base to locate the foot mat laterally within the recess.

5. The kiosk of claim 1, wherein the spacer system controls depth of the foot mat within the recess.

6. The kiosk of claim 1, further comprising a display portion for displaying information related to footcare products.

7. The kiosk of claim 1, further comprising at least one processor in communication with the foot mat, the at least one processor configured to select a footcare product for a user based on measurements for the user generated by the foot mat.

8. The kiosk of claim 7, further comprising an output device to display information received from the processor, including a footcare product recommendation for the user.

9. The kiosk of claim 1, wherein the spacer system provides underlying support for the removable cover plate.

* * * * *